(12) United States Patent
Ryklin et al.

(10) Patent No.: US 8,148,308 B2
(45) Date of Patent: Apr. 3, 2012

(54) LIQUID CLEANSING COMPOSITIONS

(75) Inventors: Irma L. Ryklin, Buffalo Grove, IL (US); James A. Faunce, North Aurora, IL (US)

(73) Assignee: Stepan Company, Northfield, IL (US)

(*) Notice: Subject to any disclaimer, the term of this patent is extended or adjusted under 35 U.S.C. 154(b) by 0 days.

(21) Appl. No.: 12/990,619

(22) PCT Filed: Apr. 30, 2009

(86) PCT No.: PCT/US2009/042318
§ 371 (c)(1),
(2), (4) Date: Jan. 6, 2011

(87) PCT Pub. No.: WO2009/135007
PCT Pub. Date: Nov. 5, 2009

(65) Prior Publication Data
US 2011/0092405 A1    Apr. 21, 2011

Related U.S. Application Data

(60) Provisional application No. 61/049,708, filed on May 1, 2008.

(51) Int. Cl.
*C11D 1/00* (2006.01)
*C11D 3/20* (2006.01)
*C11D 3/26* (2006.01)

(52) U.S. Cl. ........ 510/123; 510/124; 510/125; 510/127; 510/135; 510/138; 510/158; 510/159; 510/477; 510/488; 510/505; 510/506; 424/70.19; 424/70.21; 424/70.22; 424/70.27; 424/70.28

(58) Field of Classification Search ................ 510/123, 510/124, 125, 127, 135, 137, 138, 158, 159, 510/477, 488, 505, 506; 424/70.19, 70.21, 424/70.22, 70.27, 70.28
See application file for complete search history.

(56) References Cited

U.S. PATENT DOCUMENTS

| 5,785,979 | A  | * | 7/1998  | Wells .......................... 424/401 |
| 7,214,650 | B2 | * | 5/2007  | Kasturi et al. ................ 510/130 |
| 2002/0128162 | A1 | * | 9/2002 | Elliott et al. ................ 510/130 |
| 2003/0134759 | A1 | * | 7/2003 | Geary et al. .................. 510/119 |
| 2004/0266886 | A1 | * | 12/2004 | Seipel et al. ................. 514/712 |
| 2006/0276541 | A1 | * | 12/2006 | Tautvydas et al. ............ 514/546 |
| 2007/0289613 | A1 | * | 12/2007 | Geary et al. ..................... 134/34 |
| 2008/0051311 | A1 | * | 2/2008 | Thankachan et al. .......... 510/421 |
| 2008/0057016 | A1 | * | 3/2008 | Geary et al. ................. 424/70.11 |
| 2009/0155383 | A1 | * | 6/2009 | Kitko et al. ................... 424/642 |

FOREIGN PATENT DOCUMENTS

WO     WO2008/006076     *   1/2008

OTHER PUBLICATIONS

International Search Report and Written Opinion in PCT/US09/42318, dated Jun. 18, 2009.

* cited by examiner

*Primary Examiner* — Gregory Delcotto
(74) *Attorney, Agent, or Firm* — McAndrews, Held & Malloy, Ltd.

(57) ABSTRACT

A liquid cleansing composition comprising a glyceryl caprylate/caprate ester that provides excellent viscosity-building properties, as well as enhanced foaming properties. The glyceryl caprylate/caprate ester is preferably glyceryl caprylate/caprate, and is preferably obtained by esterifying glycerin with C8-C10 fatty acids derived from coconut or palm kernel oil. The cleansing composition also comprises one or more surfactants, and optional additives, and can be formulated into a body wash, shampoo, 2-in-1 shampoo, facial cleanser, or liquid hand soap.

17 Claims, 13 Drawing Sheets

LIQUID CLEANSING COMPOSITIONS

RELATED APPLICATIONS

The present application relates to and claims the benefit of U.S. Provisional Application No. 61/049,708 filed on May 1, 2008, incorporated by reference in its entirety.

FIELD OF THE INVENTION

The presently described technology relates to cleansing compositions. More particularly, the presently described technology relates to non-emulsion, aqueous-based liquid cleansing compositions that employ glyceryl caprylate/caprate as a thickener.

BACKGROUND OF THE INVENTION

The development of cleansing products (including, without limitation, liquid hand soaps, body washes, shampoos, 2-in-1 shampoos, bath washes, hair conditioners, facial cleansers, and the like) has long been driven by the challenge of providing a combination of performance properties such as good foaming, good cleansing, good rinsing, enhanced mildness, and improved skin feel. Often the addition of a component to a cleansing composition formulation may enhance one property to the detriment of another desired property of the composition. For example, a composition may enhance skin conditioning by incorporating emollients at the expense of foaming. Therefore, those in the relevant art have been seeking new formulations to help achieve the balance of desirable performance properties.

Recently, there has been a trend in personal care cleansing products to develop products that are mild and comprise ingredients that are naturally derived rather than synthetic. Further, there are growing concerns over the use of alkanolamides in personal care products, due to possible formation of nitrosamines. There is also an increasing desire to move away from ethylene oxide/propylene oxide (EO/PO) containing ingredients in personal care products because of the possibility of residual 1,4-dioxane being present from the processing to make the EO/PO component. Formulating liquid cleansing compositions to satisfy the trends and concerns of the industry has proved to be challenging.

Accordingly, there remains a need for a liquid cleansing formulation that provides low skin irritation, low skin drying, good cleansing ability, good foaming, and good rinsability characteristics/properties, while minimizing the use of alkanolamides and EO/PO containing components. There also remains a need for a cleansing formulation that utilizes naturally derived components that can provide multi-functional properties, thereby obtaining a desired balance of properties with fewer components, which result in lower costs of production.

SUMMARY OF THE INVENTION

The presently described technology relates to non-emulsion aqueous-based liquid cleansing compositions comprising glyceryl caprylate/caprate as a thickener and/or replacement for fatty alkanolamides. Glyceryl caprylate/caprate surprisingly imparts multifunctional performance properties to the cleansing composition, including viscosity building properties, foaming properties, improved skin-feel characteristics (e.g., skin and/or hair softness and moisturization) and mildness.

In one embodiment there is provided a liquid cleansing composition comprising at least one surfactant, at least one thickener comprising glyceryl caprylate/caprate ester, and water. The liquid cleansing composition is suitable for use as a body wash, shampoo composition, 2-in-1 shampoo, bath wash or liquid hand soap.

Further embodiments of the present invention may additionally incorporate skin conditioners, rheological modifiers, fragrances, colorants, opacifiers, pearlescent agents, herbal extracts, vitamins and the like.

While the presently described technology will be described in connection with one or more preferred embodiments, it will be understood by those skilled in the art that it is not limited to those embodiments. On the contrary, the presently described technology includes all alternatives, modifications, and equivalents as may be included within the spirit and scope of the appended claims.

DETAILED DESCRIPTION OF THE INVENTION

DETAILED DESCRIPTION OF THE INVENTION

Figure 1:
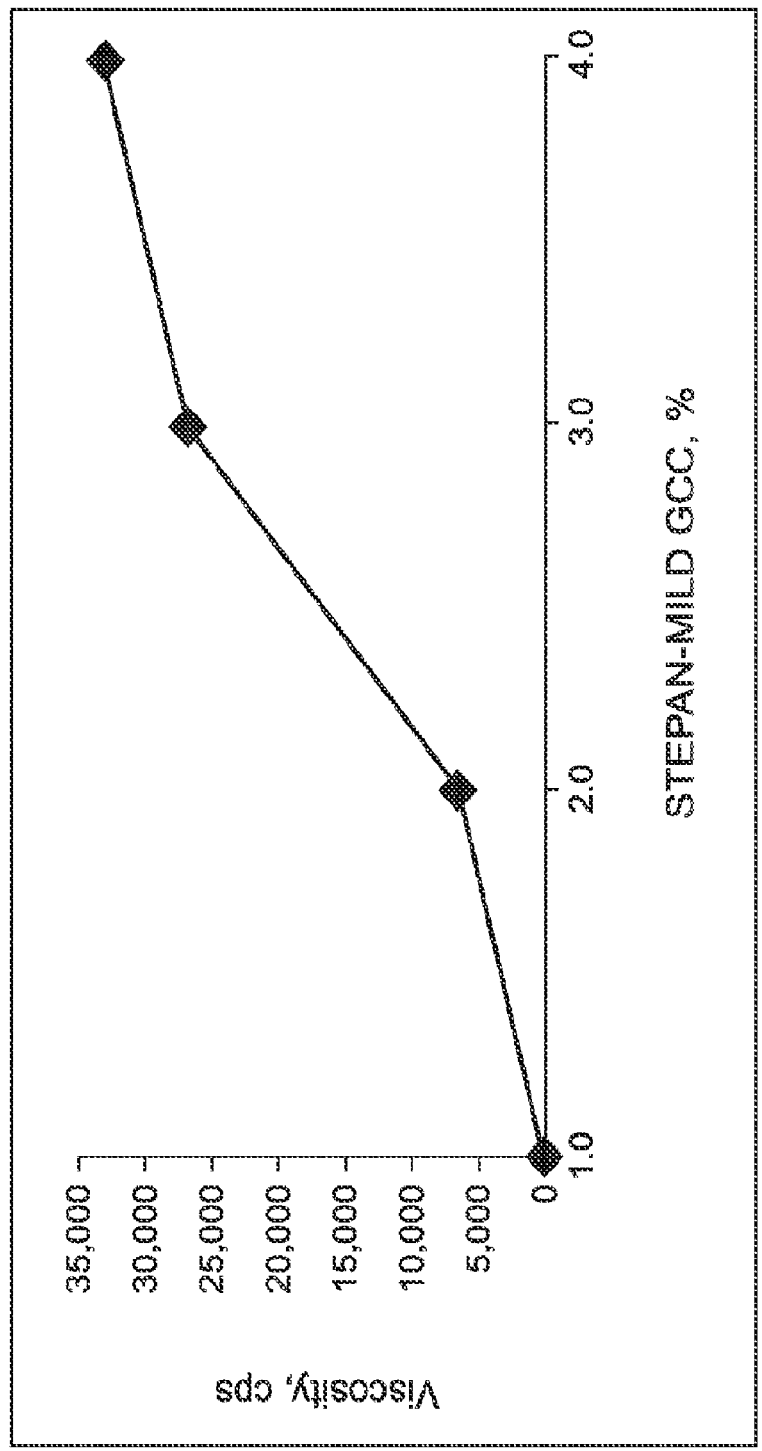
FIG. 1 is a graph illustrating the viscosity-building properties of glyceryl caprylate/caprate in sodium-based surfactant systems.

The liquid cleansing compositions of the presently described technology comprise at least one primary surfactant, a glyceryl caprylate/caprate thickener, and water. More preferably, the liquid cleansing compositions of the presently described technology comprise one or more primary surfactants, one or more secondary surfactants, the glyceryl caprylate/caprate ester, and water.

It has been unexpectedly determined that the addition of glyceryl caprylate/caprate to cleansing compositions provides not only improved viscosity-building properties, but also enhanced foaming properties. Such results are completely unexpected and surprising because typical viscosity builders utilized in personal care products are EO/PO-containing products, such as PEGs, or polymeric thickeners, such as polyquaterniums, or natural gums or celluloses. These known thickeners are of a molecular size and weight many times greater than that of glyceryl caprylate/caprate. Moreover, although glyceryl caprylate/caprate has been used as a co-emulsifier in oil-in-water or water-in-oil emulsions, it is completely unexpected that such a small molecule could impart thickening properties to a surfactant system in an aqueous-based composition that is not an emulsion.

The glyceryl caprylate/caprate ester is made by esterifying glycerin, preferably obtained from vegetable oil sources, with medium chain fatty acids, for example C8-C10 fatty acids, obtained from coconut or palm kernel oil. The resulting product comprises a mixture of mono, di- and/or triglycerides of caprylic and capric acids. Preferred glyceryl esters are mono and di-glycerides of caprylic and capric acids. A commercially available example of glyceryl caprylate/caprate can be obtained from Stepan Company, Northfield, Ill. under the trade name STEPAN-MILD GCC.

Preferably, the glyceryl caprylate/caprate comprises from about 0.1% to about 10% by weight of the total weight of a liquid cleansing composition, more preferably from about 0.2% to about 5% by weight of the total weight of a liquid cleansing composition or alternatively, the glyceryl caprylate/caprate may comprise from about 0.5% to about 4% by weight of the total weight of the composition, alternatively from about 1% to about 10% by weight of the total weight, alternatively from about 1% to about 5% by weight of the total weight, alternatively from about 1% to about 4% by weight of the total weight, alternatively from about 2% to about 5% by weight of the total weight of the composition and may include, for example, about 0.1%, about 0.2%, about 0.4%, about 0.5%, about 0.8%, about 1.0%, about 1.2%, about 1.5%, about 1.7%, about 2.0%, about 2.25%, about 2.5%, about 2.75%, about 3.0%, about 3.5%, about 4.0%, about 4.5%, about 5.0%, about 5.5%, about 6.0%, about 6.5%, about 7.0%, about 7.5%, about 8.0%, about 8.5%, about 9.0%, about 10%, and can include or involve any range or percentage inbetween including additional increments of, for example, 0.1, 0.2, 0.25, 0.3, 0.4, 0.5, 0.6, 0.7, 0.75, 0.8, 0.9 or 1.0 wt % and multiplied factors thereof, (e.g. ×1, ×2, ×2.5, ×5, ×10, ×100, etc).

The glyceryl caprylate/caprate can be incorporated into a liquid cleansing composition by mixing the component into the surfactant system used in the liquid cleansing composition. The component requires no heating in order to be formulated into the surfactant system and can be cold mixed at any step of the manufacturing process. This easy processability provides a distinct advantage over conventional EO/PO containing thickeners or amide-containing thickeners which must be heated before mixing, thereby increasing the processing steps and cost to formulate. Moreover, the glyceryl caprylate/caprate typically shows no gelation, which is an undesirable property that can occur with other viscosity-building components, such as sodium chloride.

The surfactant system used in the cleansing compositions of the present technology comprises at least one primary surfactant. Preferably, the surfactant system comprises at least one primary surfactant and at least one secondary surfactant. In some embodiments of the present technology, the surfactant system comprises one or more primary surfactants and one or more secondary surfactants.

The primary surfactant or surfactants may be a suitable anionic, nonionic, cationic, amphoteric, or zwitterionic surfactant, and preferably comprises from about 0.1% to about 70% by weight of the total cleansing composition, more preferably, from about 5% to about 60% by weight of the total cleansing composition or alternatively, the primary surfactant or surfactants can comprise from about 5% to about 50%, alternatively from about 5% to about 40%, alternatively about 5% to about 20% by weight of the total cleaning composition, and may include, for example, about 0.1%, about 0.2%, about 0.4%, about 0.5%, about 0.8%, about 1.0%, about 1.5%, about 2.0%, about 2.5%, about 3.0%, about 4.0%, about 5.0, about 7.0%, about 10%, about 12%, about 15%, about 18%, about 20%, about 25%, about 30%, about 40%, about 45%, about 50%, about 55%, about 60%, about 65%, about 70% by weight of the total weight of the cleaning composition, and can include or involve any range or percentage in-between including additional increments of, for example, 0.1, 0.2, 0.25, 0.3, 0.4, 0.5, 0.6, 0.7, 0.75, 0.8, 0.9 or 1.0 wt % and multiplied factors thereof, (e.g. ×1, ×2, ×2.5, ×5, ×10, ×100, etc).

Suitable anionic surfactants, include, without limitation: sulfonated alkyl benzene, sulfonated methyl esters, sulfonated alpha olefin, paraffin sulfonate, alkyl sulfate, alkyl alkoxy sulfate, alkyl alkoxy carboxylate, alkyl phosphate, alkyl alkoxy phosphate, alkyl sulfonate, alkyl alkoxylated sulfate, acyl lactylate, alkyl isethionate, salts thereof, and combinations thereof. Further examples can be found in "Surface Active Agents and Detergents" (Vol. I and II by Schwartz, Perry and Berch). Suitable nonionic surfactants include, without limitation: fatty acid amide, ethoxylated fatty acid amide, alkyl alcohol, alkyl alcohol ethoxylate, alkyl phenol ethoxylate, propylene glycol esters, polyglycerol esters, ethylene glycol esters, ethoxylated glycol esters, polypropylene glycol esters, alkylpolyglycoside, alkyl glucamide, and combinations thereof. More examples are generally disclosed in U.S. Pat. No. 3,929,678 to Laughlin et al., issued on Dec. 30, 1975 at column 13, line 14 through column 16, line 6, incorporated herein by reference. Cationic surfactants and cationic polymers may include, without limitation: alkyl dimethylammonium halogenide, quaternized cellulose, quaternized quar gum, esterquat, amidoquat, and stearylamidopropyl dimethyl amine quat. Other cationic surfactants useful herein are also described in U.S. Pat. No. 4,228,044 to Cambre, issued Oct. 14, 1980, incorporated herein by reference. Suitable commercially available primary surfactants include, without limitation, the STEOL® series, the ALPHA-STEP® series, including ALPHA-STEP® PC-48 (sodium methyl 2-sulfolaurate and disodium 2-sulfolaurate), BIO-TERGE® AS-40, and STEPANOL® AM-V surfactants manufactured by Stepan Company, Northfield, Ill.

Suitable secondary surfactants include for example, anionic surfactants, betaines, amine oxide, fatty acid amide, ethoxylated fatty acid amide and acyl lactylate. The secondary surfactant or surfactants may comprise from about 0.1% to about 50% by weight of the total cleansing composition, more preferably from about 1% to about 15% by weight of the total cleansing composition, or alternatively the secondary surfactant or surfactanst may comprise from about 1% to about 10% by, weight, alternatively from about 1% to about 5% by weight, alternatively from about 1.5% to about 10% by weight, alternatively from about 1.5% to about 5% by weight of the total weight of the cleaning composition, and may include, for example, about 0.1%, about 0.2%, about 0.4%, about 0.5%, about 0.8%, about 1.0%, about 1.5%, about 2.0%, about 2.5%, about 3.0%, about 4.0%, about 5.0, about 7.0%, about 10%, about 12%, about 15%, about 18%, about 20%, about 25%, about 30%, about 35%, about 40%, about 45%, about 50% by weight of the total weight of the cleaning composition, and can include or involve any range or percentage in-between including additional increments of, for example, 0.1, 0.2, 0.25, 0.3, 0.4, 0.5, 0.6, 0.7, 0.75, 0.8, 0.9 or 1.0 wt % and multiplied factors thereof, (e.g. ×1, ×2, ×2.5, ×5, ×10, ×100, etc).

Suitable commercially available secondary surfactants include, without limitation, the AMPHOSOL® series (betaines and sultaines), the ALPHA-STEP® series, including ALPHA-STEP® PC-48 (sodium methyl 2-sulfolaurate and disodium 2-sulfolaurate), and NINOL® COMF surfactants manufactured by Stepan Company, Northfield, Ill., or other surfactants disclosed and discussed below in the Examples.

The liquid cleansing compositions described herein are preferably in the form of non-emulsion liquids in which water is the principal diluent. Alternatively, although less preferred, other solvents such as alcohols may be utilized in combination with water. The level of water in a liquid cleansing composition is preferably from about 10% to about 99% by weight.

Optional Ingredients:

The formulations of the presently described technology may be used alone as a liquid cleansing composition, preferably as a body wash, hand wash, facial cleanser, shampoo or the like. Alternatively, other optional ingredients may be added to make the present compositions more preferable for a variety of different uses such as a pumpable liquid hand cleanser, 2-in-1 shampoo, gel body wash, bath wash, or the like.

For example, additional thickeners may be added if necessary to achieve a desired viscosity for a particular cleansing composition. Such thickening agents may include, for example, polymeric thickening agents, such as esterquat, amidoquat, stearylammidopropyl dimethyl amine quat, cellulosic polymers, and acrylic polymers and copolymers. Alternatively, the cleansing products may be thickened by using polymeric additives that hydrate, swell or molecularly associate to provide body, such as, for example, hydroxypropyl guar gum. Other suitable thickening agents may include, without limitation, those listed in the Glossary and Chapters 3, 4, 12 and 13 of the *Handbook of Water-Soluble Gums and Resins*, Robert L. Davidson, McGraw-Hill Book Co., New York, N.Y. 1980.

Fatty acid soaps, builders, and additional surfactants may be added to aid in cleansing ability. Emollients (including, without limitation, vegetable oils, mineral oils, silicone oils, petrolatum, polyglycarol methyl esters, and esters), skin conditioning agents (such as glycerine and free fatty acid), vitamins and herbal extracts may be added to further improve conditioning performance. Fragrances, dyes, opacifying agents, and pearlescent agents may also be added to further enhance the appearance and smell of the finished formulation. Suitable preservatives such as benzyl alcohol, methyl paraben, propyl paraben, imidazolidinyl urea and DMDM hydantoin may be utilized. Antibacterial agents such as quaternary ammonium compounds may also be utilized, although it should be noted that glyceryl caprylate/caprate itself exhibits antimicrobial properties. Furthermore, a dimethyl polysiloxane may be utilized to enhance skin feel and conditioning properties to hair.

The compositions and the methods of producing such compositions herein may be formulated and carried out such that they will have a pH of between about 4.0 to about 8.5, preferably, between about 5.0 to about 7.0. Techniques for controlling pH at recommended usage levels include the use of buffers, alkali, acids, etc., and are well known to those skilled in the art. Optional pH adjusting agents can include, but are not limited to citric acid, succinic acid, phosphoric acid, sodium hydroxide, sodium carbonate, and the like.

EXAMPLES

The following examples describe some of the preferred embodiments of the present technology without limiting the technology thereto. Other embodiments include, but are not limited to, those described in the above written description, including additional or alternative components, alternative concentrations, and additional or alternative properties and uses.

TABLE A

| Composition Trade Names & Abbreviations | |
|---|---|
| BIO-TERGE ® AS-40 CG-P | sodium $C_{14}$—$C_{16}$ olefin sulfonate |
| STEOL ® CA-230 | ammonium laureth sulfate with 2 moles ethylene oxide per mole of alcohol |
| STEOL ®33 CS-230 | sodium salt of $C_{12}$—$C_{14}$ alkyl ethoxy sulfate with 2moles ethylene oxide per mole of alcohol |
| AMPHOSOL ® HCG | cocamidopropyl betaine (CAPB) |
| AMPHOSOL ® HCA | cocamidopropyl betaine (CAPB) |
| NINOL COMF | cocamide monoethanol amine (COMEA) |
| STEPANOL ® AM | ammonium lauryl sulfate |
| STEPANOL ®WA-EXTRA | sodium lauryl sulfate |
| STEPANOL ® WAT-K | triethanolamine lauryl sulfate |
| STEPAN-MILD GCC | glyceryl caprylate/caprate |
| STEPAN-MILD L3 | lauryl lactyl lactate |
| STEPAN-MILD SL3 | Disodium laureth sulfosuccinate |
| AMPHOSOL ® 1L | Sodium lauramphoacetate |

Examples 1 and 2

Examples 1 and 2 are formulations of a sodium-based surfactant system to which glyceryl caprylate/caprate (STEPAN-MILD GCC) has been added.

TABLE B

Examples 1 and 2 (sodium-based surfactant formulations)

| | Example 1 | | Example 2 | |
|---|---|---|---|---|
| Ingredient | % active | % wt. | % active | % wt. |
| STEOL ® CS-230 | 12 | 46.6 | 14 | 54.0 |
| AMPHOSOL ® HCA or HCG | 3 | 10 | | |
| STEPAN-MILD GCC | 1.0-4.0 | 1.0-4.0 | 1.0% | 1.0% |
| D.I. Water | | Q.S. to 100 | | Q.S. to 100 |

Procedure:
1. Charge D.I. water and surfactants. Mix well.
2. Add STEPAN-MILD GCC. Mix well.

STEPAN-MILD GCC is easily mixed at ambient temperature (cold mixed) and requires no heating, unlike other thickening agents, such as EO-containing thickeners.

The Example 1 formulation containing concentrations of 1.0%, 2.0%, 3.0% and 4.0% of glyceryl caprylate/caprate were evaluated for viscosity-building properties. Viscosity was measured using a Brookfield LT, spindle #4 at 12 rpm for 60 seconds. The results are shown in FIG. 1.

As can be seen in FIG. 1, the STEPAN-MILD GCC component can be cold blended with a sodium-based surfactant system and provides excellent viscosity-building properties without the addition of sodium chloride. An amount of 2% by weight of the STEPAN-MILD GCC component can provide a viscosity of greater than about 6,000 cps, and an amount of 3% by weight surprisingly yields a viscosity of about 25,000 cps. Viscosities in the range of about 10,000 to 15,000 cps are desirable for personal cleansing compositions, and viscosities in the range of about 15,000 to 25,000 are even more preferable.

Example 3

The surfactant system from Example 1 (CS-230/HCG) was prepared without the STEPAN-MILD GCC component to use as a control formulation. The Example 1 formulation (with the STEPAN-MILD GCC component) and the control formulation were then evaluated for hand wash foaming and softness using an in-vivo human expert panel.

At least six panelists with different skin types (dry, normal, and moist) were chosen for each test. The skin type of the panelist was determined using a NOVA meter. A NOVA reading less than 100 represents dry skin, 110-130, normal skin and 130 or above, moist skin. The panelists were asked to assess the performance of the Example 1 formulation and the control in a blind test using a 1 to 5 rating scale, with 1 being the worst and 5 being the best. Panelists were not told which samples were the Example 1 formulation, and which samples were the control.

Panelists were asked to assess the following characteristics during and after the washing procedure: foam volume, skin softness, skin dryness, and tackiness during drying. To identify tackiness during drying, the panelists were instructed that some products may impart a sticky/tacky feel on the skin during the transition from a wet to a dry stage. Tackiness can be assessed by touching the fingers of the same hand together or by force required to separate fingers. To identify skin tightness when dry, the panelists were instructed that some products may leave the skin feeling tight or stretched after the skin is completely dry. The panelists were instructed that this property should not be evaluated until the panelist is sure that the hands are completely dry. Similarly, skin dryness was evaluated once the hands were completely dry.

To identify skin softness, the panelists were instructed to characterize how soft and smooth the skin feels to the touch. A product can often leave the skin feeling dry, but smooth. The positive extreme would be a smooth velvety feel (ranking of 5 on a 1-5 scale), and the opposite would be a rough feeling skin with some grittiness (ranking of 1 on a 1-5 scale). All samples were coded in order to get a fair comparison between the experimental and control products.

Human Panel Test Method
1. Panelists were asked to pre-wash their hands with 15% active sodium lauryl sulfate solution to remove residue from the skin and establish the baseline before evaluating of experimental liquid cleansing products.
2. Hand washing tests were conducted using luke-warm (95° F. and 105° F.) running tap water.
3. Using a syringe, 1 ml of the test product was dispensed to the panelist's wet palm.
4. The panelists were asked to wash their hands by gently rubbing them together for 30 seconds followed by rinsing under running tap water for 15 seconds.
5. The washing procedure was repeated and the foam generated was collected and measured using a graduated beaker prior to rinsing.
6. The panelists were asked to rank the product for wet properties using a 1-5 scale.
7. The hands were dried using a paper towel, and then evaluated for wet to dry stage transition properties.
8. Skin feel evaluation was done at ambient temperature (~25° C.).

Figure 2:
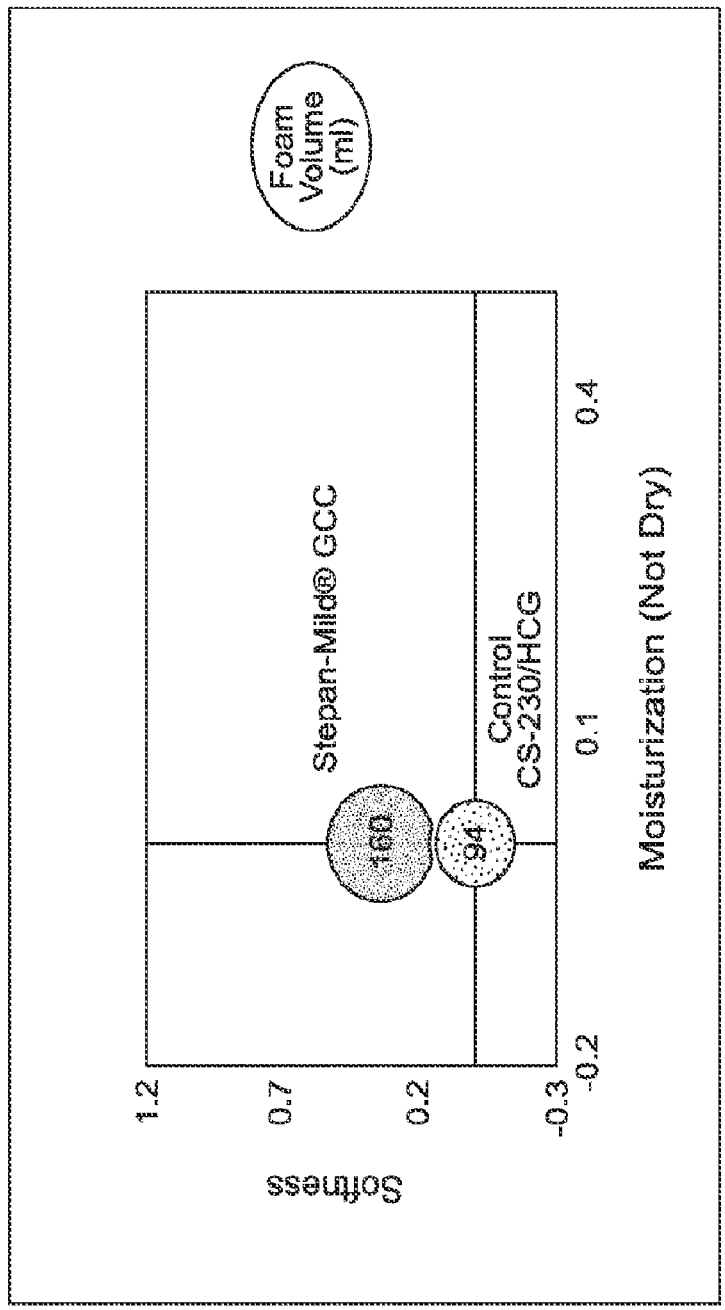
FIG. 2 is a bubble chart comparing the foaming properties of a composition in accordance with the present technology with the foaming properties of a control composition.

The average response for the panelists, for the experimental formulation, is subtracted from the average response for the control formulation. A positive score indicates that the experimental formulation outperformed the control. The results for the comparison of the Example 1 formulation with the control formulation are shown in the bubble graph of FIG. 2. As illustrated in FIG. 2, the Example 1 formulation, in accordance with the present technology, gives directionally better softness compared to the control formulation.

The volume of foam collected in the graduated beakers of each of the formulations was also measured and compared. The measured volume in ml is indicated in each of the bubbles shown in the FIG. 2 bubble chart. As illustrated in FIG. 2, the Example 1 formulation of the present technology had a foam volume of 160 ml, whereas the control formulation had a foam volume of only 94 ml.

Example 4

The viscosity-building properties of the STEPAN-MILD GCC glyceryl caprylate/caprate were evaluated in alternative surfactant systems. The surfactant systems used for this example are set forth below in Table C.

TABLE C

Alternative Surfactant Systems

| Run No. | Surfactant System (4:1 Ratio, 15 Total Weight % Active) |
|---|---|
| 1 | BIO-TERGE AS-40 CG/AMPHOSOL ® HCA |
| 2 | STEPANOL ® WA-EXTRA/AMPHOSOL ® HCA |
| 3 | STEPANOL ® AM/AMPHOSOL ® HCA |
| 4 | STEPANOL ® WAT-K/AMPHOSOL ® HCA |
| 5 | STEOL ® CS-230/AMPHOSOL ® HCA |

Figure 3:
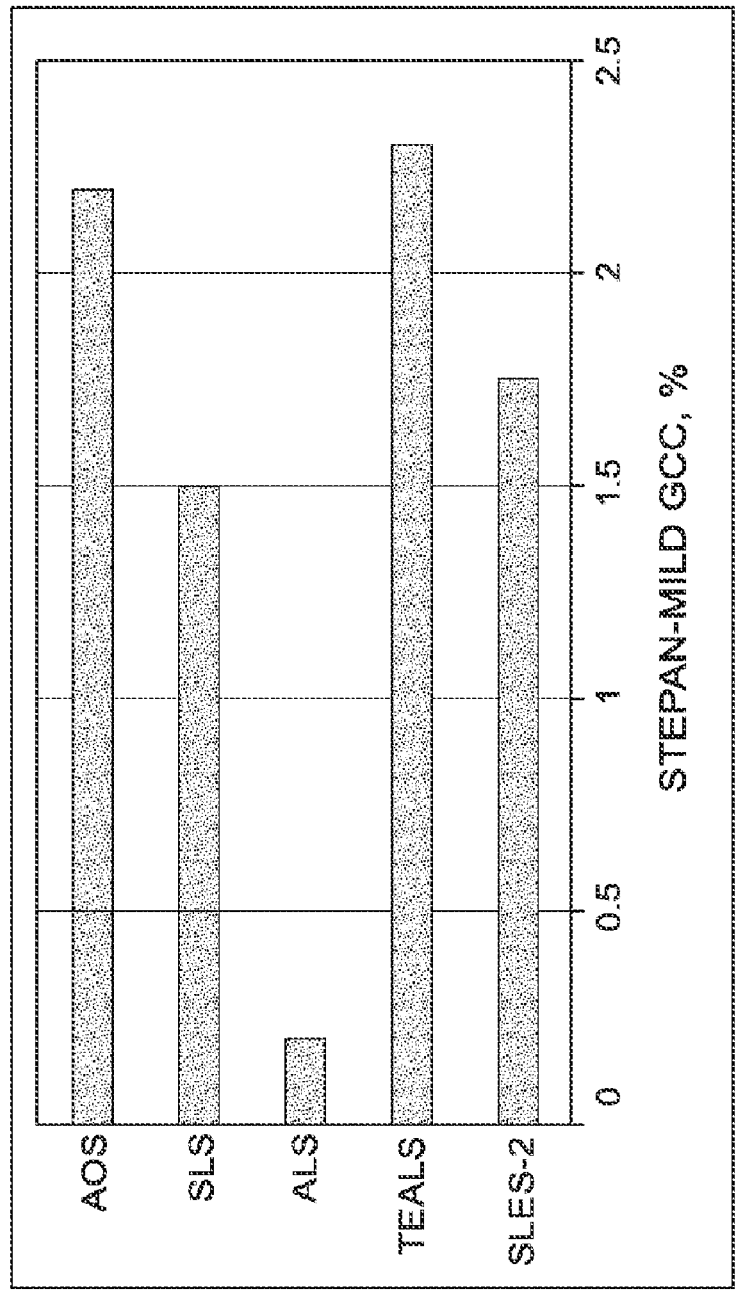
FIG. 3 is a graph illustrating the amount of glyceryl caprylate/caprate ester required to thicken different surfactant/CAPB systems to about 6,000 cps.

The STEPAN-MILD GCC component was added to each of the surfactant systems in Table C in an amount sufficient to achieve a viscosity of 6,000 cps for each formulation. The amount of the STEPAN-MILD GCC component added to each surfactant system is graphically illustrated in FIG. 3. As can be seen in FIG. 3, the amount of glyceryl caprylate/caprate added to achieve a viscosity of about 6,000 cps can range from about 0.25% by weight to about 2.25%, depending upon the surfactant system utilized.

Example 5

Comparative

The Example 2 formulation was prepared except that commercially available, known thickening components containing varying amounts of ethylene oxide (EO) and carbon chains were substituted for the STEPAN-MILD GCC component. Specifically, 1% by weight of a thickener containing 150 EO molecules (PEG-150 distearate), 120 EO molecules (PEG-120 methyl glucose dioleate) and 18 EO molecules (PEG-18 glyceryl oleate/cocoate), respectively, were each substituted for the STEPAN-MILD GCC component.

Figure 4:
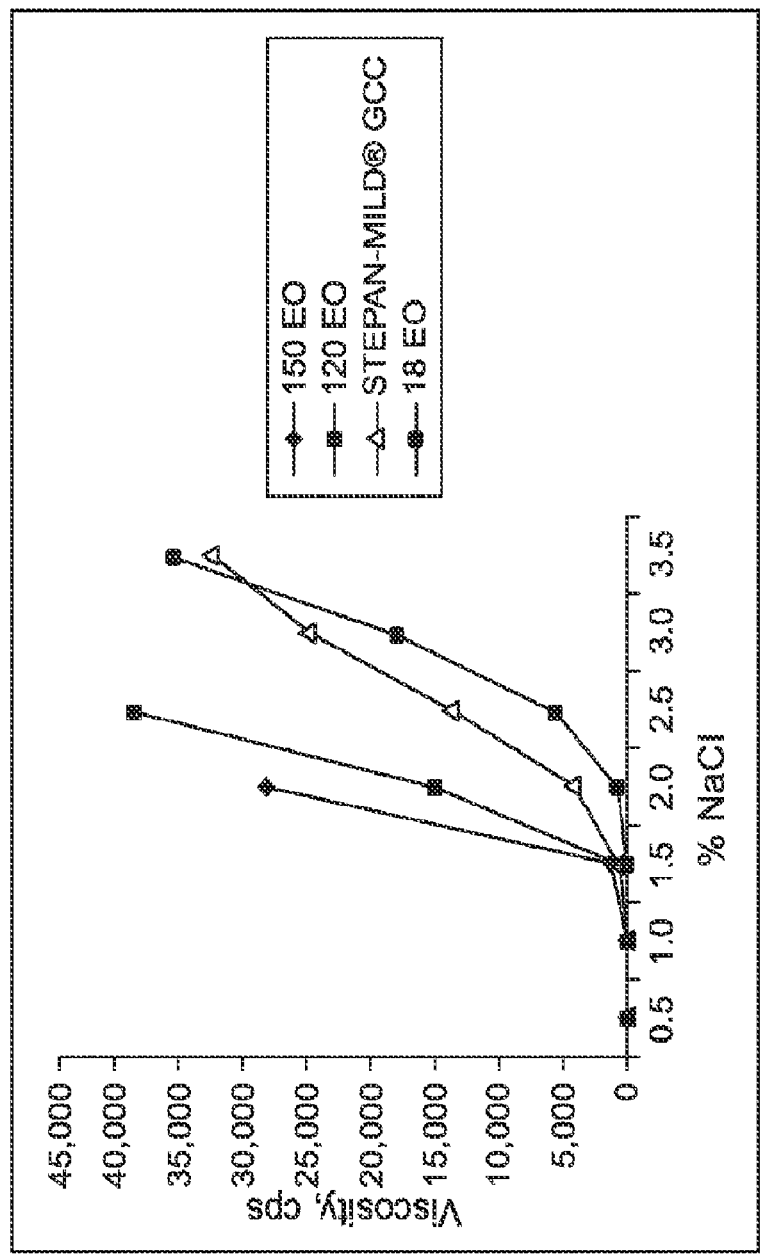
FIG. 4 is a graph comparing the viscosity-building properties of glyceryl caprylate/caprate of the present technology with known EO-containing thickening agents.

Different concentrations of sodium chloride (NaCl) salt ranging from 0% to 3.5% by weight were added to the surfactant systems containing the different EO-containing thickeners, as well as the Example 2 formulation containing the STEPAN-MILD GCC component, to determine the effect of salt concentration on the viscosity profile of the surfactant system at 1% thickener concentration. The results are shown graphically in FIG. 4. As can be seen from the FIG. 4 graph, small amounts of sodium chloride (e.g., 2-3%) added to the Example 2 formulation, containing 1% by weight glyceryl caprylate/caprate, can result in a viscosity that is comparable or better than the viscosity obtained using known EO-containing thickeners.

Example 6

Shake Foam Test

A standard shake foam test with and without 2% by weight castor oil was performed on each of the formulations prepared in Example 5.

Figure 5:
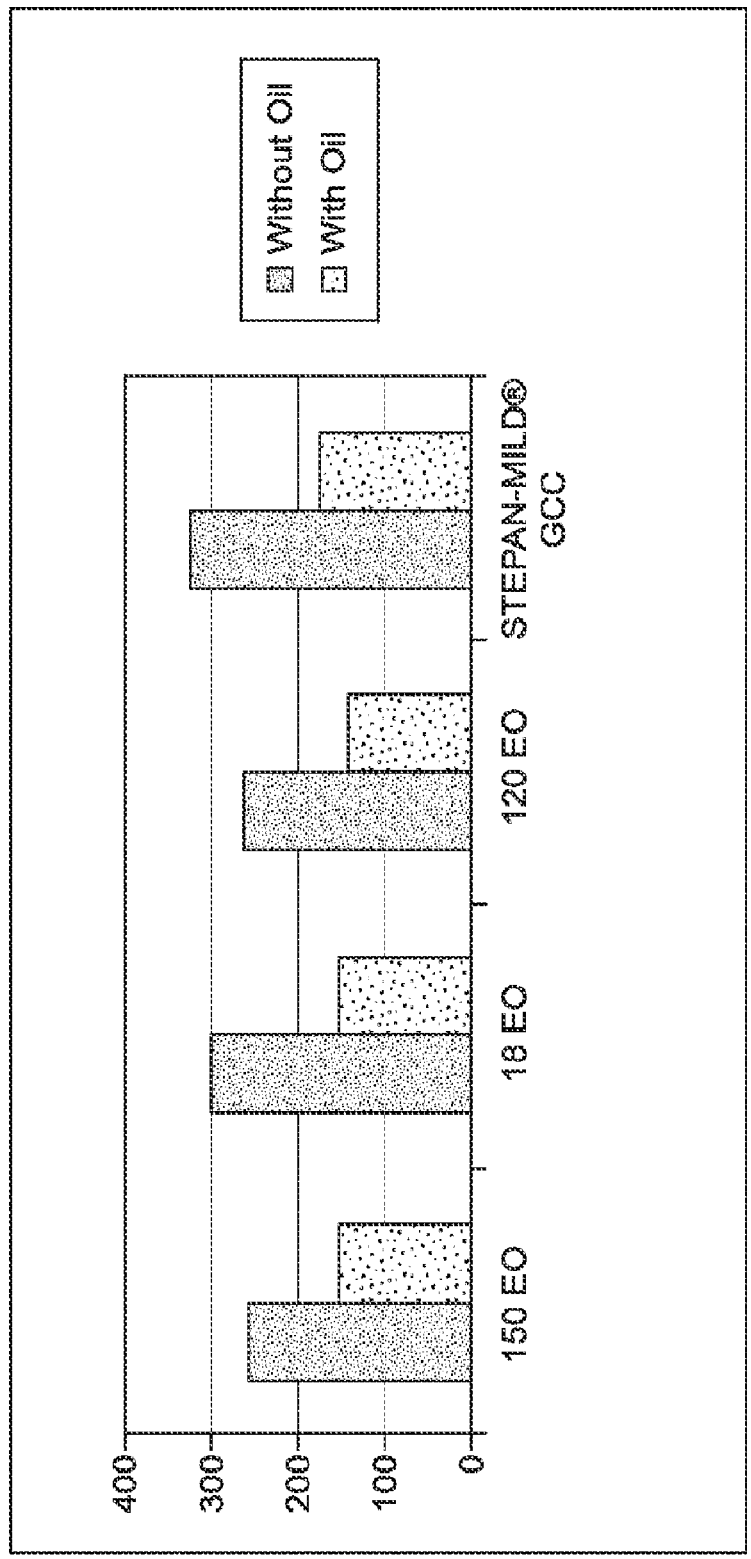
FIG. 5 is a graph comparing the foaming profile of glyceryl caprylate/caprate of the present technology with the foaming profiles obtained using known EO-containing thickening agents.

The foaming profiles of each of the formulations were evaluated and the results of the foaming test are graphically illustrated in FIG. 5. As can be seen from the FIG. 5 graph, the addition of the STEPAN-MILD GCC component gives improved foaming performance compared to the known thickening components.

Example 7

Figure 6:
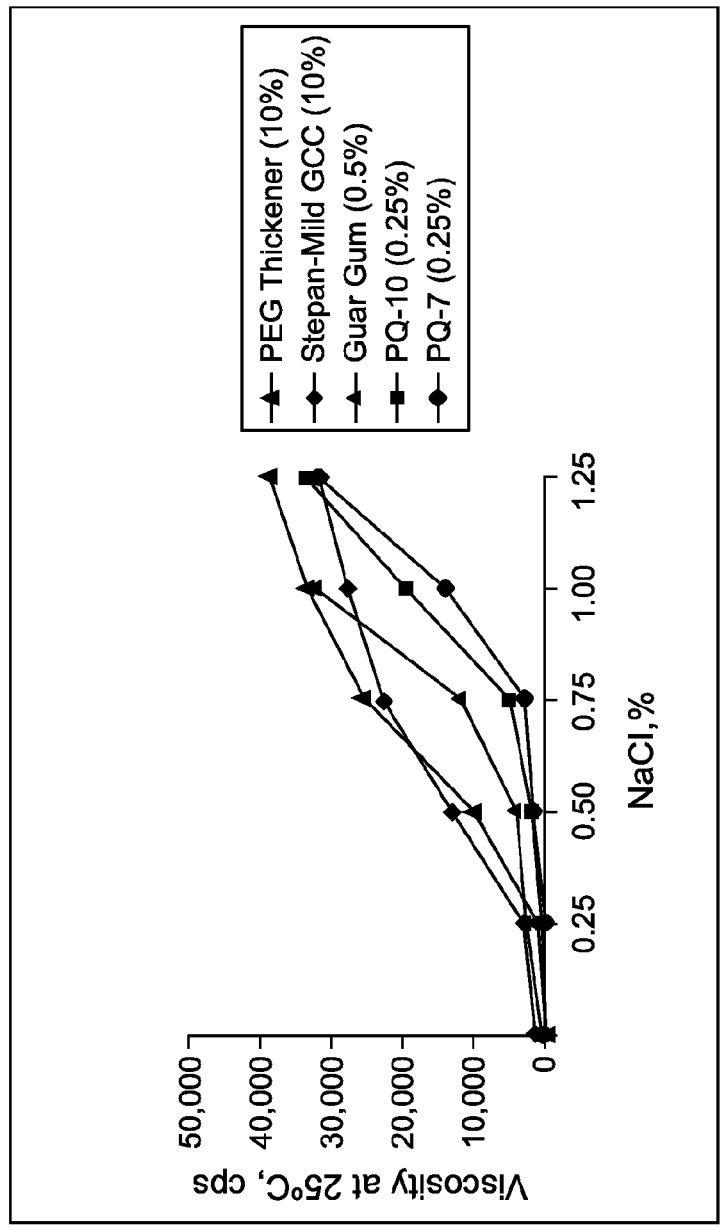
FIG. 6 is a graph comparing the viscosity-building properties of glyceryl caprylate/caprate of the present technology with known thickening agents.

The Example 1 formulation was prepared except that commercially available thickening agents were substituted for the STEPAN-MILD GCC glyceryl caprylate/caprate component in the surfactant system. Specifically, formulations were prepared with 1% by weight of a commercially available PEG thickener, with 0.5% by weight of a guar gum thickener, with 0.25% by weight of a commercially available Polyquaternium-10 thickener, and with 0.25% by weight of a commercially available Polyquaternium-7 thickener. Different concentrations of sodium chloride salt ranging from 0% to 1.25% by weight were added to each of the formulations, including the Example 1 formulation, to determine the viscosity-building properties of the formulations. The results are shown graphically in FIG. 6. As can be seen from the FIG. 6 graph, the STEPAN-MILD GCC component provides excellent viscosity-building properties that are comparable or better than those obtained with other, commercially available, thickening agents.

Example 8

Shake Foam Test

Figure 7:
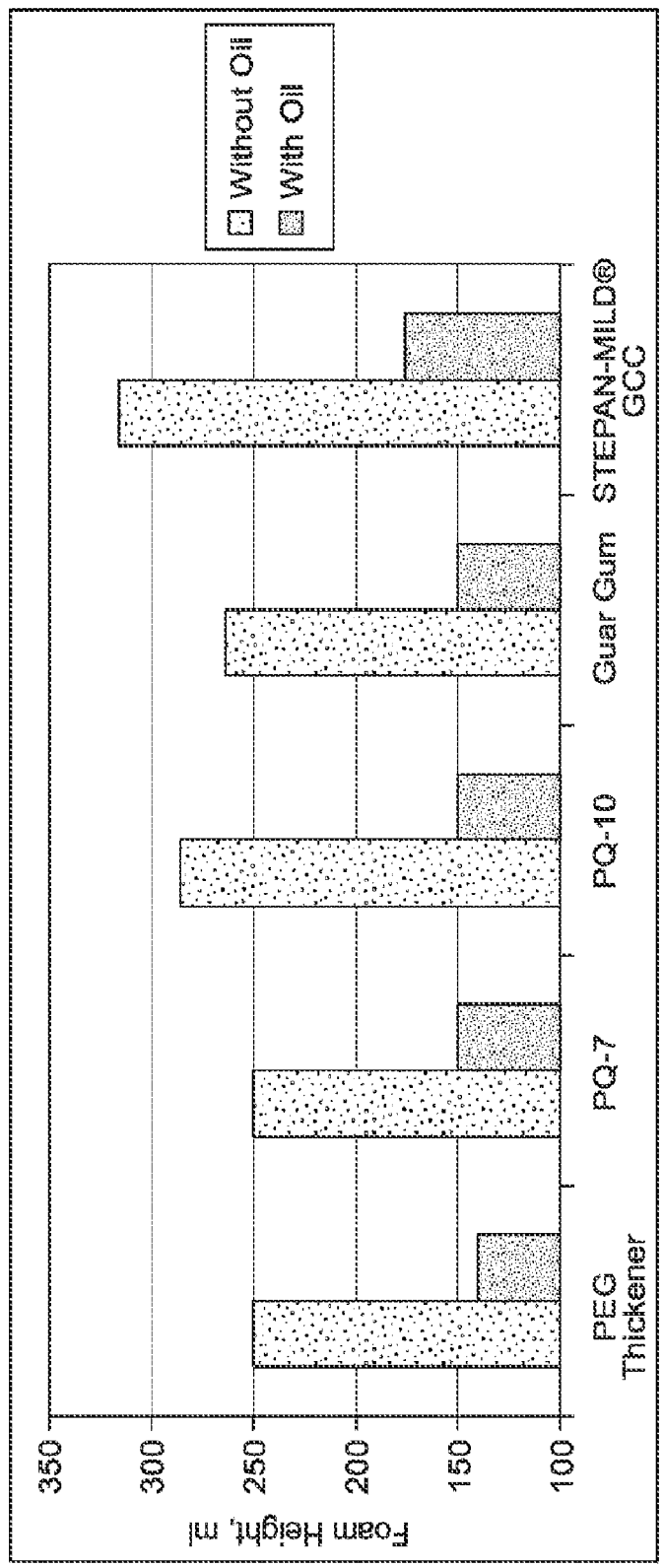
FIG. 7 is a graph comparing the foaming profile of glyceryl caprylate/caprate with the foaming profiles obtained using known thickening agents.

A standard shake foam test with and without 2% by weight castor oil was performed on each of the formulations prepared in Example 7. The foaming profiles of each of the formulations were evaluated, and the results of the foaming test are shown graphically in FIG. 7. As can be seen from the FIG. 7 graph, the addition of the STEPAN-MILD GCC component gives improved foaming performance compared to the other known thickeners.

Examples 9 and 10

Figure 8:
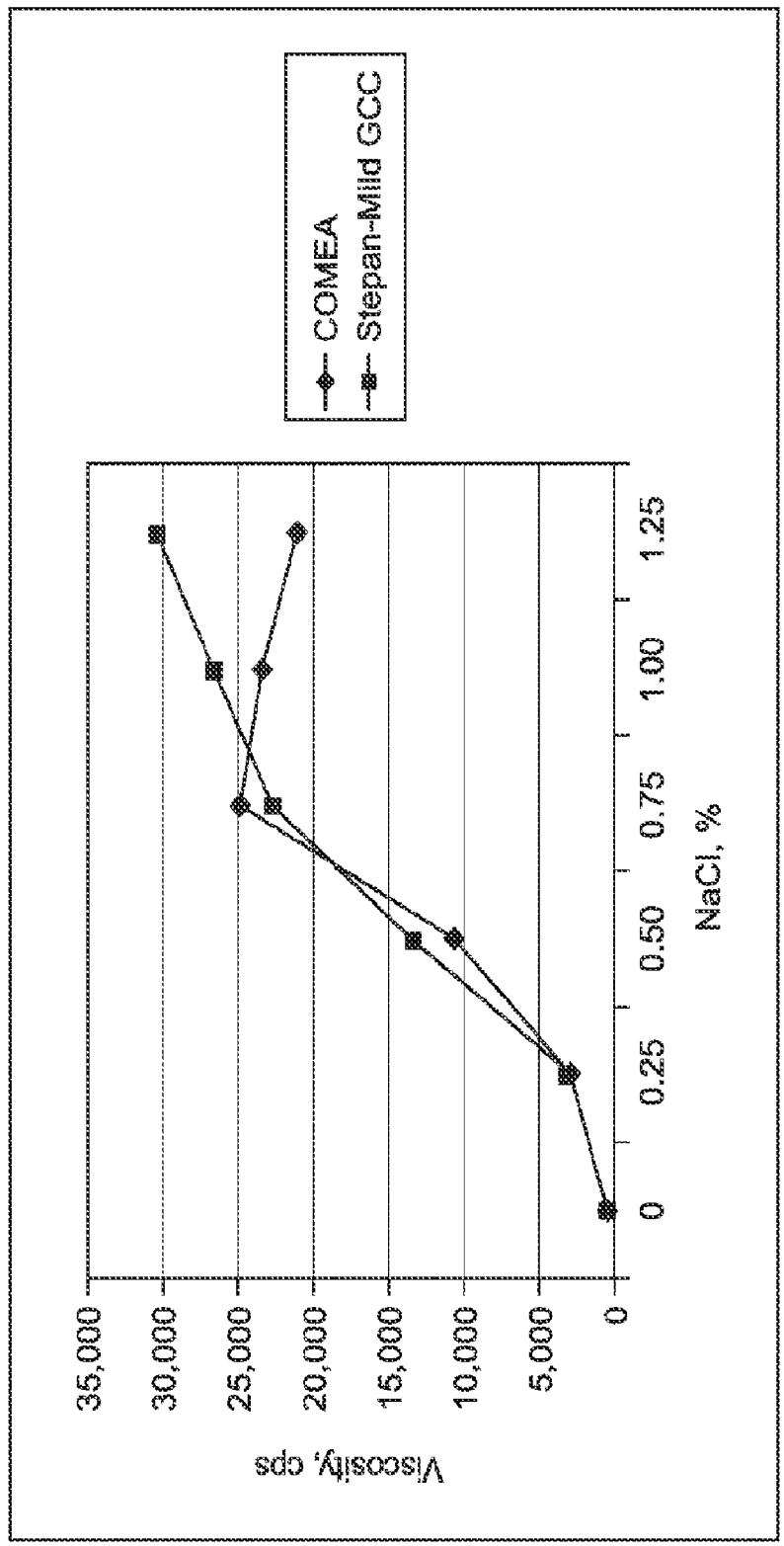
FIG. 8 is a graph comparing the viscosity-building properties of glyceryl caprylate/caprate with the viscosity-building properties of cocamide monoethanol amine (COMEA) in a sodium laureth sulfate/cocoamidopropyl betaine surfactant system.

For Examples 9 and 10, the formulations of Examples 1 and 2 were prepared except that 1% by weight of cocamide monoethanolamine (COMEA) was substituted for the STEPAN-MILD GCC component in each of the formulations. Different amounts of sodium chloride ranging from 0% to 1.25% by weight were added to the Example 1 formulation and the formulation containing COMEA (Example 9), and different amounts of sodium chloride salt ranging from 0% to 3.0% by weight were added to the Example 2 formulation and the formulation containing COMEA (Example 10). The viscosity-building properties of the Example 1 formulation and the COMEA formulation containing the same STEOL® CS-230/AMPHOSOL® HCA surfactant system were evaluated and compared. The results are shown in FIG. 8. Similarly, the viscosity-building properties of the Example 2 formulation and the COMEA formulation containing the same STEOL® CS-230 surfactant system were evaluated and compared. The results are shown in FIG. 9.

Figure 9:
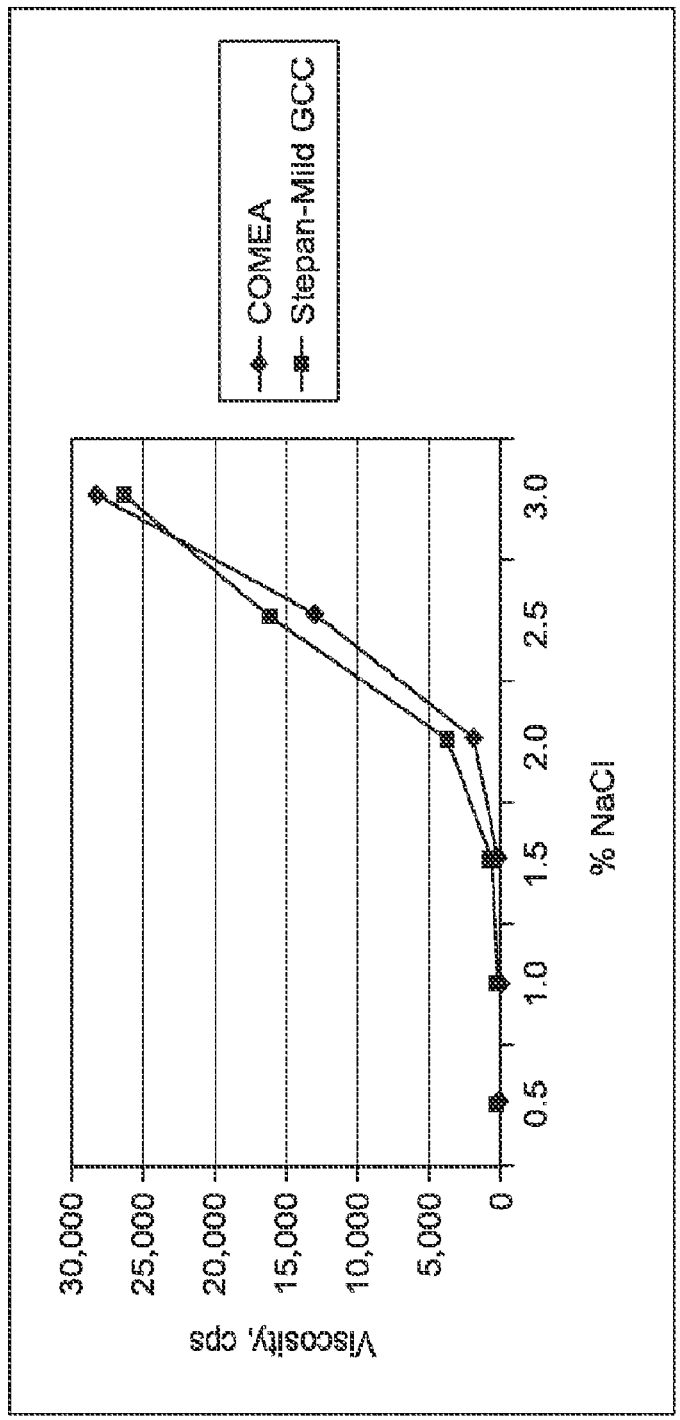
FIG. 9 is a graph comparing the viscosity-building properties of glyceryl caprylate/caprate with the viscosity-building properties of cocamide monoethanolamine (COMEA) in a sodium laureth sulfate surfactant system.

As can be seen from the FIG. 8 and FIG. 9 graphs, the formulations of Example 1 and Example 2 exhibit viscosity-building properties that are comparable to those of the COMEA formulations. Moreover, the Example 1 and 2 formulations of the present technology achieve excellent viscosity without the use of nitrosamines. Thus, the STEPAN-MILD GCC component addresses industry safety concerns over the use of nitrosamines in personal care products.

Example 11

Shake Foam Test

Figure 10:
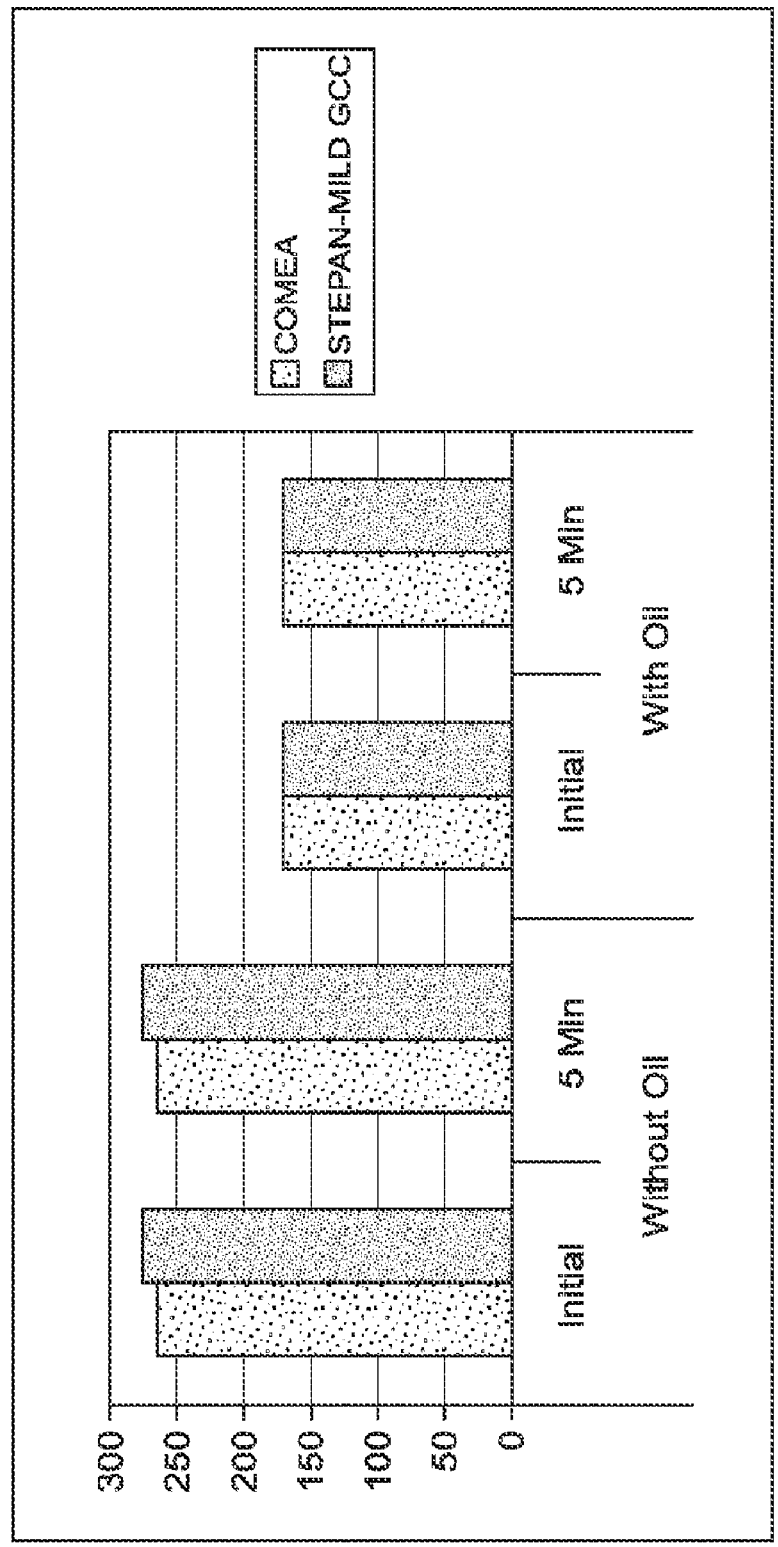
FIG. 10 is a graph comparing the foaming profile of glyceryl caprylate/caprate with the foaming profile obtained with COMEA.

The formulations from Example 10 (STEPAN-MILD GCC and COMEA each in a STEOL® CS-230 surfactant system) were evaluated in a standard shake foam test with and without 2% by weight castor oil. The foaming profiles for each of the formulations are shown in FIG. 10. As can be seen from FIG. 10, the STEPAN-MILD GCC component and the COMEA component provide comparable flash foam and foam stability properties.

Example 12

Figure 11:
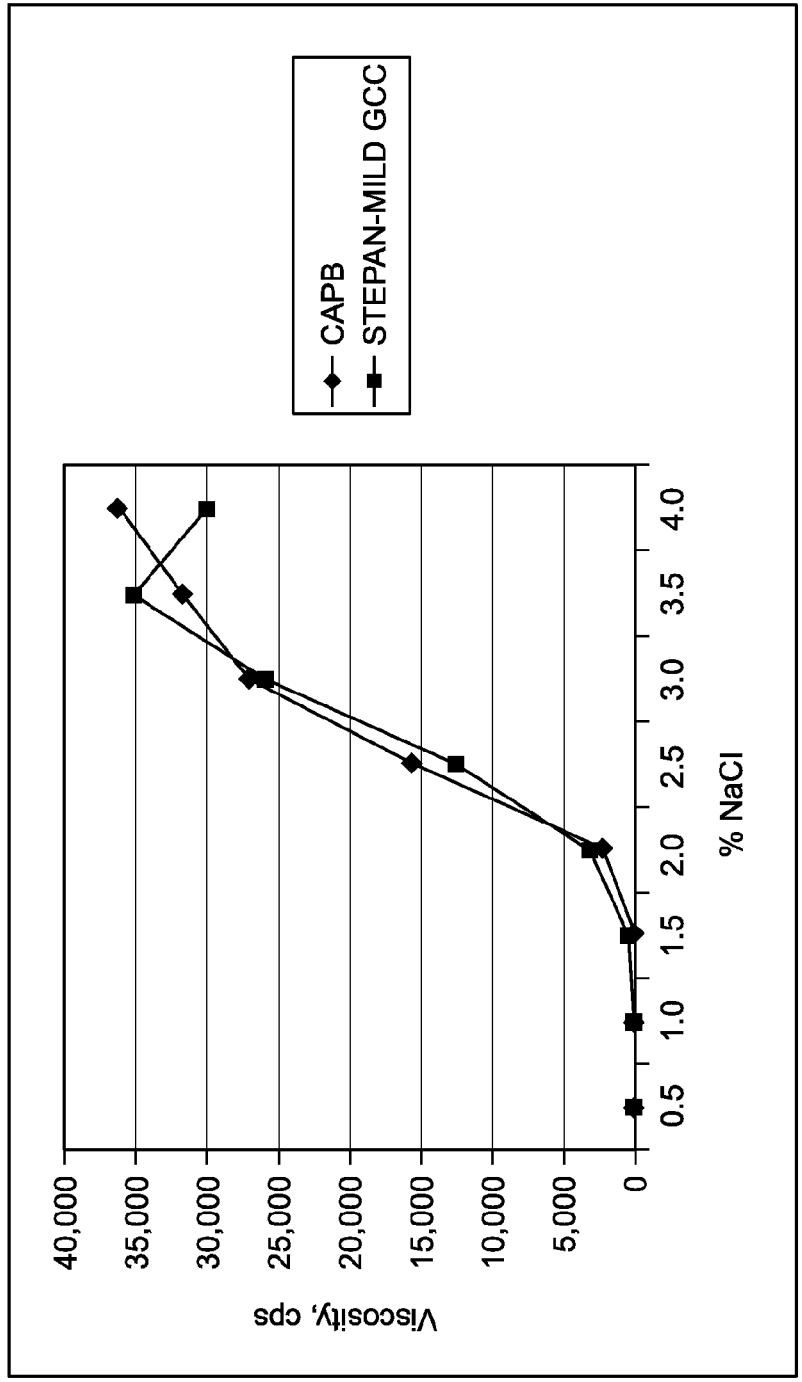
FIG. 11 is a graph comparing the viscosity building properties of glyceryl caprylate/caprate and betaine in a sodium laureth sulfate surfactant system.

The Example 2 formulation was prepared except that 1% by weight of a betaine was substituted for the STEPAN-MILD GCC glyceryl caprylate/caprate component. Different concentrations of sodium chloride salt ranging from 0% to 4.0% by weight were added to the Example 2 formulation and the betaine-containing formulation to determine the viscosity building properties of the formulations. The results are shown graphically in FIG. 11. As can be seen from the FIG. 11 graph, the STEPAN-MILD GCC component provides excellent viscosity-building properties that are comparable to those obtained when a betaine is added to the surfactant system.

In addition to the surfactants disclosed above, particular alkyl lactyllactates can be incorporated into various compositions, including liquid cleansing compositions, and used as surfactants, emulsifiers, skin feel agents, film formers, rheological modifiers, solvents, release agents, lubrication agents, conditioners, and dispersants, etc. Such alkyl lactyllactates, processes for preparing them and compositions comprising them, are further disclosed in PCT application Nos. PCT/US07/72975 and PCT/US07/72937, both filed on Jul. 6, 2007, which are hereby incorporated by reference in their entirety.

An alkyl lactyllactate, in particular lauryl lactyllactate (L3), made in accordance with the above-referenced PCT applications, was used in combination with STEPAN-MILD GCC to determine the effect of STEPAN-MILD GCC on the viscosity-building properties of L3. The evaluation of the combination of STEPAN-MILD GCC and L3 is described in Example 13.

Example 13

Formulations were prepared by mixing 12% by weight active STEOL® CS-230 surfactant and 0.8% by weight lauryl lactyllactate (L3), and adding varying amounts of STEPAN-MILD GCC to the surfactant and L3 mixture. The formulations that were prepared are set forth below in Table D:

TABLE D

| Ingredient | Sample 1 % Active | Sample 2 % Active | Sample 3 % Active | Sample 4 % Active | Sample 5 % Active |
|---|---|---|---|---|---|
| STEOL ® CS-230 | 12% | 12% | 12% | 12% | 12% |
| L3 | 0.8% | 0.8% | 0.8% | 0.8% | 0.8% |
| STEPAN-MILD GCC | — | 0.25% | 0.5% | 0.75% | 1.0% |
| D.I. Water | Q.S. to 100 | Q.S. to 100 | Q. S. to 100 | Q.S. to 100 | Q.S. to 100 |

Figure 12:
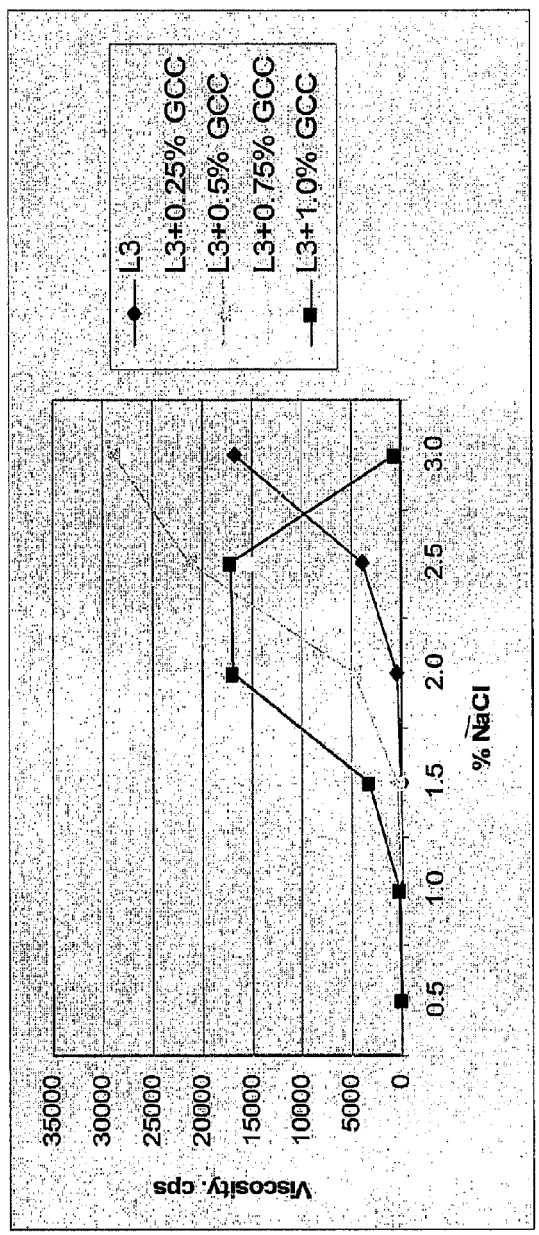
FIG. 12 is a graph illustrating the effect of glyceryl caprylate/caprate on the viscosity-building properties of lauryl lactyl lactate (L3) in a sodium laureth sulfate surfactant system.

Different concentrations of sodium chloride salt ranging from 0% to 3% by weight were added to the samples prepared above to determine the viscosity-building properties of the samples. The results are shown in the graph of FIG. 12. As can be seen in the FIG. 12 graph, increasing the amount of STEPAN-MILD GCC generally allows a shift of the viscosity curve towards a lower amount of salt required to build viscosity to the desired value.

Example 14

In this experiment, the viscosity-building properties of STEPAN-MILD GCC glyceryl caprylate/caprate were compared with the viscosity-building properties of other secondary surfactants in a sodium laureth sulfate/cocamidopropyl betaine surfactant system. The formulations that were prepared are set forth below in Table E:

Procedure:
1. Charge D.I. water, STEOL® CS-230 and AMPHOSOL HCA. Mix well.
2. Add tested products. Mix until clear.
3. Adjust pH.

Figure 13:
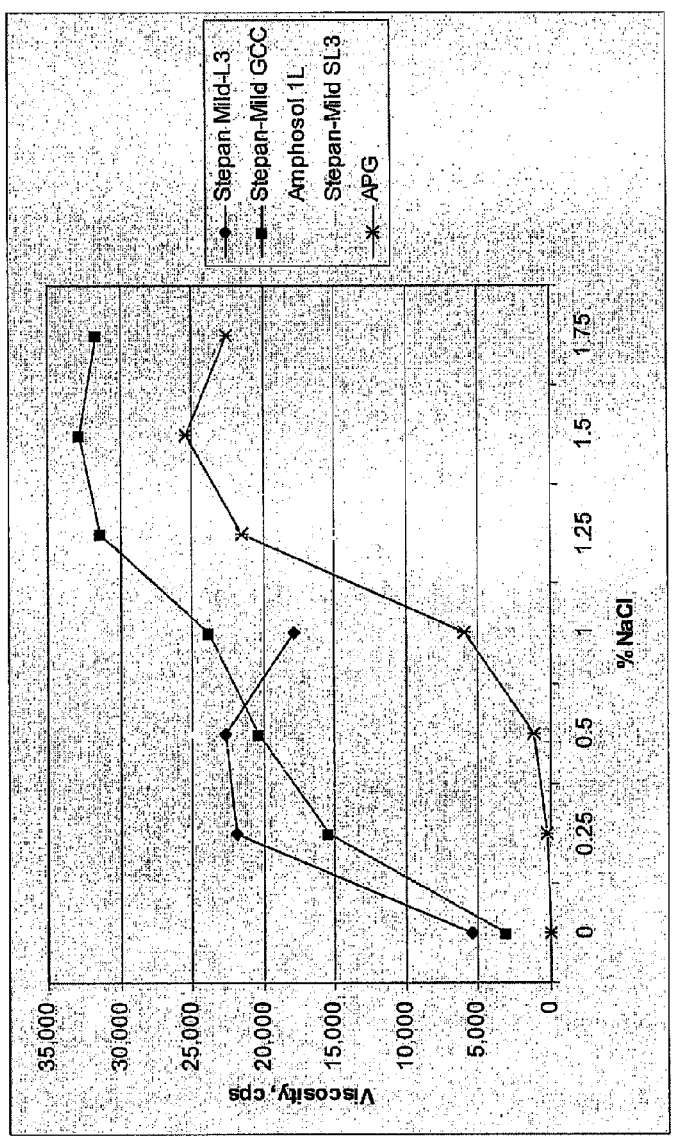
FIG. 13 is a graph comparing the viscosity-building properties of glyceryl caprylate/caprate with secondary surfactants in a sodium laureth sulfate/CAPB surfactant system.

Different concentrations of sodium chloride salt ranging from 0% to 1.75% by weight were added to the samples prepared above to evaluate and compare the viscosity-building properties of the samples. The results are shown in the graph of FIG. 13. As can be seen from the graph, STEPAN-MILD GCC is comparable or better than other secondary surfactants in viscosity-building properties. Further, STEPAN-MILD GCC can be used by itself or in combination with other secondary surfactants to achieve desired viscosities for the liquid cleansing compositions.

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

What is claimed is:

1. A liquid cleansing composition comprising:
   (a) at least one surfactant;
   (b) glyceryl caprylate/caprate wherein the glyceryl caprylate/caprate comprises a mixture of glyceryl mono and di-caprylate and glyceryl mono and di-caprate; and
   (c) water, wherein the liquid cleansing composition is not an emulsion.

2. The liquid cleansing composition of claim 1, wherein the surfactant is selected from the group consisting of an anionic surfactant, an amphoteric surfactant, a non-ionic surfactant, a cationic surfactant, a zwitterionic surfactant, and mixtures thereof.

3. The liquid cleansing composition of claim 1, wherein the glyceryl caprylate/caprate is present in the composition in an amount of about 0.1% to about 10% by weight of the total weight of the composition.

4. The liquid cleansing composition of claim 1, wherein the glyceryl caprylate/caprate is present in the composition in an amount of about 0.2% to about 5% by weight of the total weight of the composition.

5. The liquid cleansing composition of claim 1, wherein the composition further comprises one or more additives selected

TABLE E

| Ingredient | % Active | % Weight per 100 | Sample 1 | Sample 2 | Sample 3 | Sample 4 | Sample 5 |
|---|---|---|---|---|---|---|---|
| Water D.I. | | | 85 | 85 | 81.46 | 81 | 83 |
| Steol ® CS-230 | 12 | 46.3 | 92.7 | 92.7 | 92.7 | 92.7 | 92.7 |
| AMPHOSOL HCA | 3 | 10.16 | 20.3 | 20.3 | 20.3 | 20.3 | 20.3 |
| STEPAN-MILD L3 | 1 | 1 | 2 | | | | |
| STEPAN-MILD GCC | 1 | 1 | | 2 | | | |
| AMPHOSOL 1L (36% active) | 1 | 2.77 | | | 5.54 | | |
| STEPAN-MILD SL3-BA (33.25% active) | 1 | 3.0 | | | | 6 | |
| Alkylpolyglucosides (APG) | 1 | 2.0 | | | | | 4 |
| Citric acid (50%) | | q.s. to pH 5.5-5.7 | | | | | |
| TOTAL | | | 200 | 200 | 200 | 200 | 200 |
| Appearance | | | Clear | Clear | Clear | Clear | Clear |
| pH as is/adjusted | | | 6.9/5.5 | 7.3/5.63 | 9.09/5.66 | 5.75/5.6 | 7.52/5.62 | from the group consisting of fragrances, dyes, vitamins, herbal extracts, preservatives, opacifying agents, pearlescent agents, thickeners, emollients, foam builders, pH. adjusters and antibacterial agents.

6. The liquid cleansing composition of claim 1, wherein the composition comprises at least one primary surfactant and at least one secondary surfactant.

7. The liquid cleansing composition of claim 6, wherein the primary surfactant is present in an amount of about 0.1% to about 70% by weight of the cleansing composition.

8. The liquid cleansing composition of claim 6, wherein the primary surfactant is present in an amount of about 5.0% to about 60% by weight of the cleansing composition.

9. The liquid cleansing composition of claim 6, wherein the secondary surfactant is present in an amount of about 0.1% to about 50% by weight of the cleansing composition.

10. The liquid cleansing composition of claim 6, wherein the secondary surfactant is present in an amount of about 1.0% to about 15% by weight of the cleansing composition.

11. The liquid cleansing composition of claim 6, wherein the secondary surfactant is selected from the group consisting of betaines, amine oxides, hydroxysultaines, sulfosuccinates, amphoacetates, sarcosinates, and acyl lactylates.

12. The liquid cleansing composition of claim 2, wherein the anionic surfactant is selected from the group consisting of sulfonated alkyl benzene, sulfonated methyl esters, sulfonated alpha olefin, paraffin sulfonate, alkyl sulfonate, alkyl alkoxy sulfate, alkyl alkoxy carbonate, alkyl phosphate, alkyl alkoxy phosphate, alkyl sulfonate, alkyl alkoxylated sulfate, acyl lactylate, alkyl isethionate, salts thereof, and combinations thereof.

13. A liquid cleansing composition comprising:
(a) from about 0.1% to about 70% by weight of at least one surfactant;
(b) from about 0.1% to about 10% by weight of glyceryl caprylate/caprate wherein the glyceryl caprylate/caprate comprises a mixture of glyceryl mono and di-caprylate and glyceryl mono and di-caprate; and
(c) water, wherein the liquid cleansing composition is not an emulsion.

14. The liquid cleansing composition of claim 13, wherein the glyceryl caprylate/caprate is glyceryl caprylate/caprate prepared by reacting glycerin with C8-C10 fatty acids derived from coconut or palm kernel oil.

15. The liquid cleansing composition of claim 13, wherein the composition comprises at least one primary surfactant and at least one secondary surfactant.

16. The liquid cleansing composition of claim 13, wherein the composition further comprises one or more additives selected from the group consisting of fragrances, dyes, vitamins, herbal extracts, preservatives, opacifying agents, pearlescent agents, thickeners, emollients, foam builders, pH. adjusters and antibacterial agents.

17. The liquid cleansing composition of claim 13, wherein the composition further comprises an alkyl lactyllactate.

* * * * *